United States Patent [19]
Messner et al.

[11] Patent Number: 6,081,336
[45] Date of Patent: Jun. 27, 2000

[54] MICROSCOPE CALIBRATOR

[75] Inventors: Dale A. Messner, Uniontown; Ruhul Quddus; John D. Schellenberg, both of Cleveland Heights, all of Ohio

[73] Assignee: Picker International, Inc., Highland Heights, Ohio

[21] Appl. No.: 08/938,116

[22] Filed: Sep. 26, 1997

[51] Int. Cl.[7] .................................................. G01B 11/14
[52] U.S. Cl. ...................... 356/375; 356/243.4; 359/368; 250/559.29; 606/130; 128/653.1
[58] Field of Search ..................................... 356/153, 138, 356/143, 250, 243.4, 375; 606/166, 167, 170, 172, 130; 33/281, 282, 283, 286; 250/201.3, 252.1, 559.29; 359/382, 383, 368, 385

[56] References Cited

U.S. PATENT DOCUMENTS

| | | | |
|---|---|---|---|
| 4,055,376 | 10/1977 | Daberko | 356/243.4 |
| 4,609,814 | 9/1986 | Nobuaki et al. | 356/400 |
| 4,722,056 | 1/1988 | Roberts et al. . | |
| 4,836,667 | 6/1989 | Ozeki | 359/393 |
| 4,836,778 | 6/1989 | Baumrind et al. | 433/69 |
| 4,968,147 | 11/1990 | Shoemaker | 356/153 |
| 5,305,091 | 4/1994 | Gelbart et al. | 356/375 |
| 5,309,913 | 5/1994 | Kormos et al. | 606/130 |
| 5,383,454 | 1/1995 | Bucholz . | |
| 5,513,005 | 4/1996 | Müller . | |
| 5,517,990 | 5/1996 | Kalfas et al. . | |
| 5,622,170 | 4/1997 | Schulz | 356/375 |
| 5,662,111 | 9/1997 | Cosman | 128/653.1 |
| 5,694,212 | 12/1997 | Weissman | 359/393 |

FOREIGN PATENT DOCUMENTS

| | | |
|---|---|---|
| 01102306 | 4/1989 | Japan . |
| WO 96/07144 | 3/1996 | WIPO . |
| WO 96/11624 | 4/1996 | WIPO . |

OTHER PUBLICATIONS

"A Frameless Stereotaxic Operating Microscope for Neurosurgery", Eric M. Friets, et al.; IEEE Transactions on Biomedical Engineering, vol. 36, No. 6, Jun. 1989 pp. 608–617.

"A frameless stereotaxic integration of computerized tomographic imaging and the operating microscope", David W. Roberts, M.D., et al.; J. Neurosurg; vol. 65; Oct. 1986; pp. 545–549.

*Primary Examiner*—Hoa Q. Pham
*Attorney, Agent, or Firm*—Timothy B. Gurin; John J. Fry; Eugene E. Clair

[57] ABSTRACT

A microscope calibrator includes a housing supporting a series of focusing targets each situated at a predetermined distance from one another. Attributes of the microscope are determined by focusing the microscope on one ore more of the focusing targetrs and determining a location of the microscope with respect to the focusing targets focused upon. The position of the focusing targets are determinable by virtue of a local reference frame target attached to the microscope calibrator or by using a tracked probe to communicate the location of each point focused upon by the microscope on each of the focusing targets.

9 Claims, 9 Drawing Sheets

MICROSCOPE CALIBRATOR

TECHNICAL FIELD

The present invention relates to the medical diagnostic and surgical arts. More particularly the present invention relates to a microscope calibrator for calibrating a microscope used in conjunction with various medical procedures including neurosurgery, neurobiopsy, CT-table needle body biopsy, breast biopsy, endoscopic procedures, orthopedic surgery, and the like.

BACKGROUND OF THE INVENTION

Three-dimensional diagnostic images of the brain, spinal cord, and other body portions are produced by diagnostic imaging equipment such as CT scanners, magnetic resonance imagers, and the like. These imaging modalities often provide structural detail with a resolution of a millimeter or better.

Image guided surgery systems have been developed to utilize this data to assist the surgeon in presurgical planning and in accurately locating a region of interest within the body of a patient. In the operating arena, the image guided surgery systems are used to display position and orientation of a surgical tool in its correct location with respect to the images of the patient. One example of an image guided surgery system is U.S. Pat. No. 5,517,990, Stereotaxy Wand and Tool Guide, to Kalfas et al. issued May 21, 1996, incorporated by reference herein.

In order to further aid the surgeon in viewing an area of interest within the patient's body, a high powered surgical microscope is often utilized. Such a microscope may, for instance, be used to see blood vessels or other microscopic details within the patient. The microscope is supported by a movable electronic support structure which may be rolled along the ground or mounted to a ceiling or a wall, for example. Controls adjacent the microscope on the support structure allow the surgeon to manually or electronically position the microscope over the patient's body at a desired location.

In order to track the location of the microscope within the surgical room or other area, a series of position signaling devices such as infrared emitters or reflectors are typically secured to the microscope at some location. The position signaling devices are tracked by a localizer located within the surgical room capable of sensing the position signaling devices. The image guided surgery system uses this data to provide the surgeon with an indication of the position and orientation of the microscope with respect to patient data and images. Such precise tracking of the microscope is helpful to ensure the surgeon knows in exactly what direction the microscope should be moved to see an area of interest.

Unfortunately, calibrating or determining attributes of a microscope such that a viewing area of the microscope is properly tracked with respect to images displayed on a monitor is often a nuisance. For instance, each time the microscope is accidently bumped or otherwise shaken the microscope attributes typically needs to be re-calibrated. This is true in part because upon being bumped the position indicators attached to the microscope are also often moved or dislocated. Because the microscope is tracked with respect to the location of the position indicators, such movement causes errors in tracking which can lead the surgeon to focus on an incorrect location within a patient. Further, if the microscope is bumped or jarred during a surgical procedure, the surgeon may need to take time away from the procedure to re-calibrate the microscope.

The present invention provides a new and improved method and apparatus for calibrating and verifying calibration of various attributes of a surgical microscope which addresses the above-referenced matters, and others.

SUMMARY OF THE INVENTION

A microscope calibrator includes a housing supporting a series of focusing targets each situated at a predetermined distance from one another. Attributes of the microscope are determined by focusing the microscope on one ore more of the focusing targetrs and determining a location of the microscope with respect to the focusing targets focused upon. The position of the focusing targets are determinable by virtue of a local reference frame target attached to the microscope calibrator or by using a tracked probe to communicate the location of each point focused upon by the microscope on each of the focusing targets.

In a preferred embodiment, the microscope calibrator includes the reference frame target attached thereon. The reference frame target is tracked by cameras in an operating room or other area. The reference frame target is connected to a pivotable shaft in which a series of focusing targets are located. The pivotable shaft provides for easy manipulation of the shaft so that the microscope can be aligned therewith. Information related to an offset between the reference frame target and each of the focusing targets is preloaded in a memory of a computer system or passed along from a memory chip coupled to the reference frame target or in some other way. Based on information obtainable from the cameras tracking the reference frame target and based on the known offset information, the microscope is rapidly calibrated such that the computer system knows the exact orientation of the microscope in the tracked area and the operator knows a center of a depth of field of the microscope.

In an alternative embodiment of the present invention, the microscope calibrator includes a series of focusing targets situated at different levels on a housing. In this embodiment a tracked probe is used to communicate location information of each of the focusing targets focused on by the microscope to the computer system. Again, rapid and complete calibration of the microscope may be achieved by virtue of having known spaced apart focusing targets on which the microscope can focus.

In accordance with an aspect of the present invention, a tool for determining an attribute of a microscope is provided. The tool includes a plurality of focusing targets, and a means for supporting the plurality of focusing targets in a spaced relation.

In accordance with another aspect of the present invention, a system for determining an attribute of a microscope is provided. The attribute is related to an object in an image guided surgery system. The system includes a tool, and means for determining a location of the tool in relation to the object. The tool includes a plurality of focusing targets and a means for supporting the plurality of focusing targets.

In accordance with still another aspect of the present invention, a method of determining an attribute of a microscope is provided. The method includes the steps of focusing the microscope on a first focusing target, focusing the microscope on a second focusing target situated a different focusing distance from the microscope than the first focusing target, communicating a location of the first focusing target and the second focusing target to a processor; and communicating a location of the microscope to the processor.

It is an object of the present invention to provide a tool capable of quickly and reliably determining a focusing distance of a microscope.

It is another object of the present invention to provide a tool capable of accurately determining a line of sight of the microscope.

It is yet another object of the present invention to provide a tool capable of calibrating a rotational sense of the microscope.

It is still another object of the present invention to provide a tool capable of determining a focusing distance, line of sight, and rotational sense of a microscope all at once.

To the accomplishment of the foregoing and related ends, the invention then, comprises the features hereinafter fully described and particularly pointed out in the claims. The following description and the annexed drawings set forth in detail certain illustrative embodiment of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE PREFERRED EMBODIMENTS

The present invention will now be described with reference to the drawings in which like reference numerals are used to refer to like elements throughout.

Figure 1:
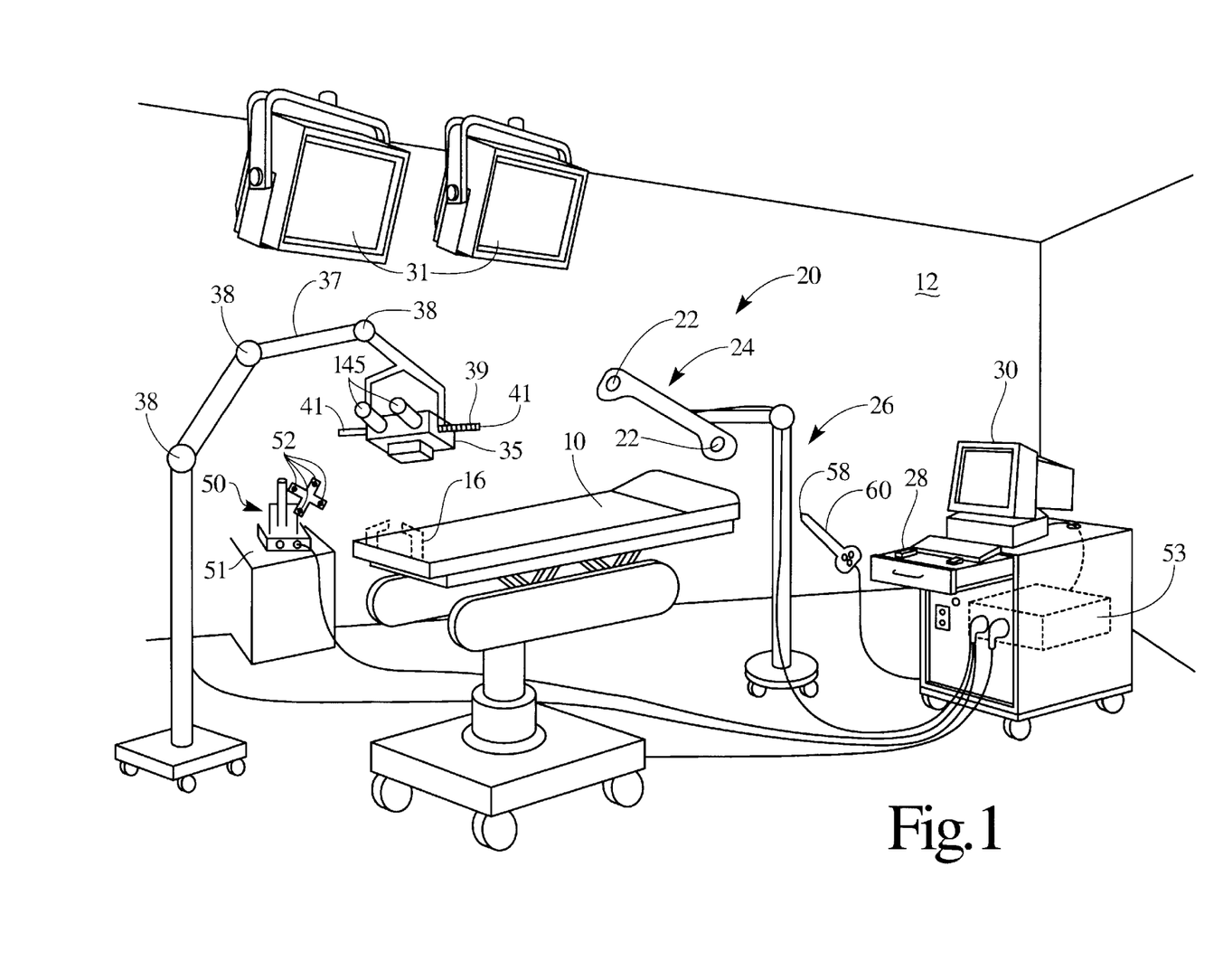
FIG. 1 is a perspective view of an operating room in which the present invention is deployed.

With reference to FIG. 1, a patient (not shown) is received on an operating table or other subject support 10 and appropriately positioned within an operating or surgical room 12. A securing means such as a head clamp 16 securely positions a portion of the patient or subject under consideration. A locating device 20 such as an infrared localizer determines the location and orientation of at least one surgical tool. Tools refers to any instrument or apparatus in the surgical room which is tracked by the locating device 20.

In the preferred embodiment, the locating device 20 is an infrared localizer such as the Polaris™ localizer system supplied by Northern Digital, Inc. of Waterloo, Ontario, Canada. The localizer system includes two spaced apart infrared cameras 22 mounted on a sensor head 24. The sensor head 24 is in turn mounted in a fixed position within the operating room 12, for example on a stand 26 resting on the floor. The cameras 22 may be mounted in another known position in the operating room 12, such as to the ceiling or wall or to the subject support 10. Of course, other locating devices, such as ultrasonic, optical, RF, or electromagnetic localizers, may be used. The surgical tool may also be mounted to an articulated arm, the arm functioning as the locating device.

A surgical microscope 35 aids a surgeon in viewing microscopic images of the patient while conducting a procedure or surgery. The microscope 35 is supported by a microscope support structure 37 which is situated on the floor. The microscope support structure 37 includes several movable joints 38 which may be manually or electronically controlled to position the microscope 35 in a desired location. For instance, control buttons 39 attached to a handle 41 of the microscope 35 may be used to accurately and precisely locate the microscope 35 in the operating room 12. A reference frame target 36 (see FIG. 7) including three or more position signaling devices 36a is rigidly attached to the microscope 35. The position signaling devices may, for instance, be spaced apart infrared emitters such as light-emitting diodes (LED's). The position signaling devices provide a means for the locating device 20 to accurately track a plane in which the microscope 35 is positioned. Although the microscope support structure 37 is shown to be situated on the floor, it will be appreciated that the microscope support structure could alternatively be attached to the ceiling or to a wall. Of course, the microscope 35 could be supported by any other suitable mechanism. The focusing distance of the microscope 35 may be of fixed length or may be variable in nature. In the event the focusing distance of the microscope 35 is of fixed length, an operator would need to physically move the entire microscope 35 via the microscope support structure 37 in order to bring objects of interest into and out of view. If the focusing distance is variable, the operator would have an option of varying the focusing distance of the microscope 35 to the extent possible or physically moving the microscope to bring objects into focus.

A surgical microscope calibrator 50 is situated on a table 51 in the operating room 12 in proximity to the microscope 35. As will be discussed in more detail below, the microscope calibrator 50 provides a means for rapidly and accurately calibrating the microscope 35.

Figure 2:
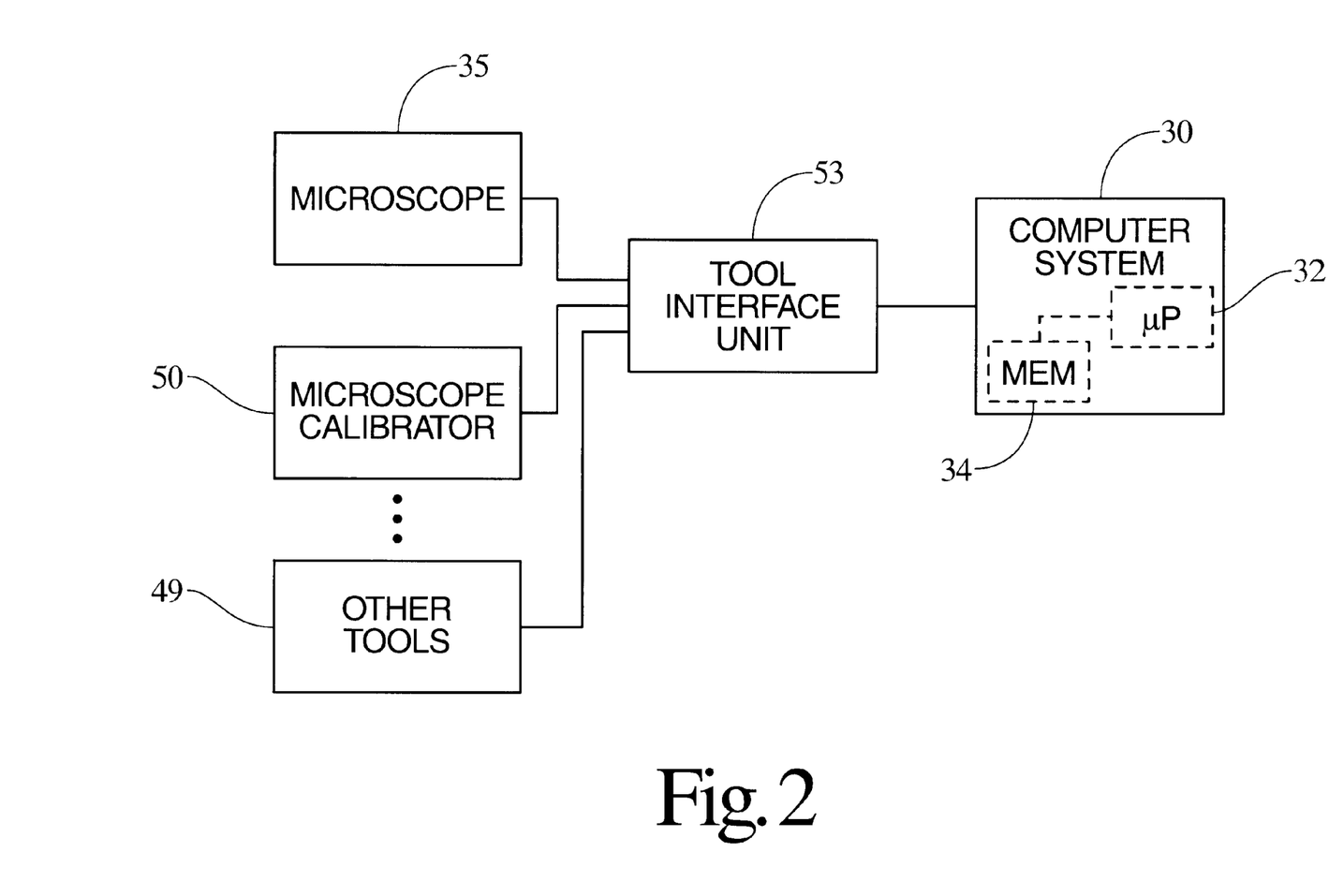
FIG. 2 is a block diagram of a system according to the present invention.

With continued reference to FIG. 1 and further reference to FIG. 2, an operator console 28 houses a computer system 30. Alternately, the computer system 30 can be remotely located and connected with the operator console 28 by cabling. The computer system 30 includes a processor 32 and a data memory 34 coupled to the processor 32. The data memory 34 contains data indicative of a three-dimensional image of the patient or subject. Because the data can be visualized as a three-dimensional rectangular grid, selectable orthogonal and other oblique planes of the data can be readily withdrawn from the data memory 34 using conventional technology. Such data may be displayed on an overhead monitor 31 in the operating room 12 for convenient viewing by the surgeon.

The microscope 35, the microscope calibrator 50, and other tools 49 are coupled to the computer system 30 through a tool interface unit 55. The tool interface unit 55 serves to interface the computer system 30 with all the tools in the operating room 12.

Each tool in the operating room passes along information related to its local reference frame to the tool interface unit 55. For instance, the local reference frame for the microscope calibrator 50 may be defined such that an origin is at some desirable location associated with the microscope calibrator 50. Based on signals detected by the cameras 22, the location and orientation of the microscope calibrator 50 and hence the local reference frame with respect to the cameras 22 and hence the operating room reference frame are determined. Similarly, the relationship between the local reference frames of the other tools and the operating room reference frame may be determined.

In the event the three or more position signaling devices secured to the patient or other apparatus is not physically coupled to the tool interface unit 55 such that information related to the orientation of the three or more position signaling devices can be passed along, it is necessary to correlate or register the reference frames. This is accomplished by touching a tip 58 of a tracked surgical tool or probe 60 to the at least three reference points defined in relation to the patient or other apparatus and determining the location and orientation of the probe 60 at each point.

Based on this information the transforms between the patient, tools and operating room reference frames can readily be calculated. As is well known in the art, a transform is accomplished by determining an offset $x_{offset}$, $y_{offset}$, $z_{offset}$ between the reference frames to be transformed. These values of $x_{offset}$, $y_{offset}$, $z_{offset}$ are added to or subtracted from the coordinates of one of the reference frames as required to translate between the two. The coordinate systems are then rotated relative to each other about their origins by angles $\alpha$, $\beta$, $\gamma$ so that their respective x, y and z axes coincide.

Figure 3:
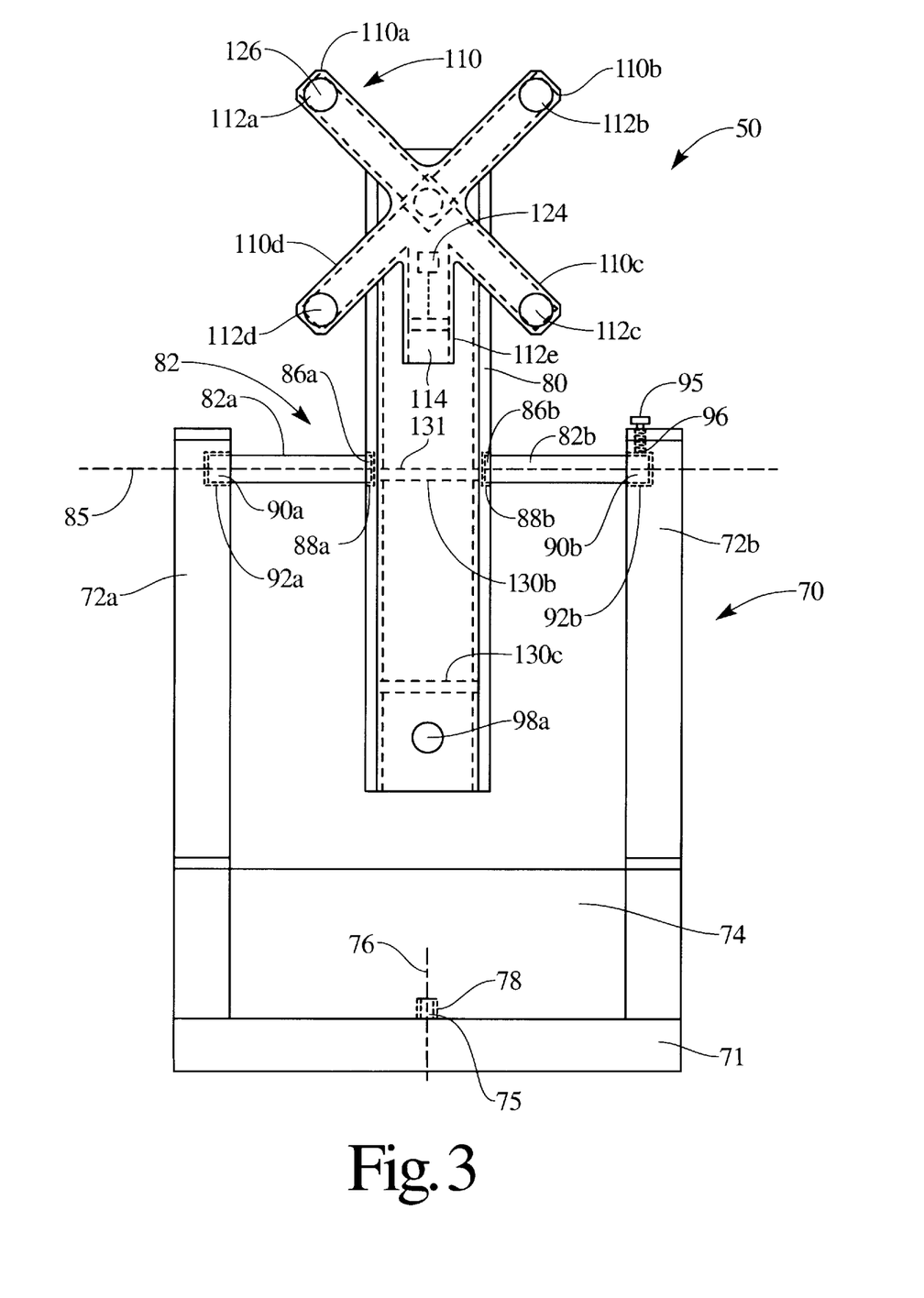
FIG. 3 is a front view of a microscope calibrator of the present invention.
Figure 4:
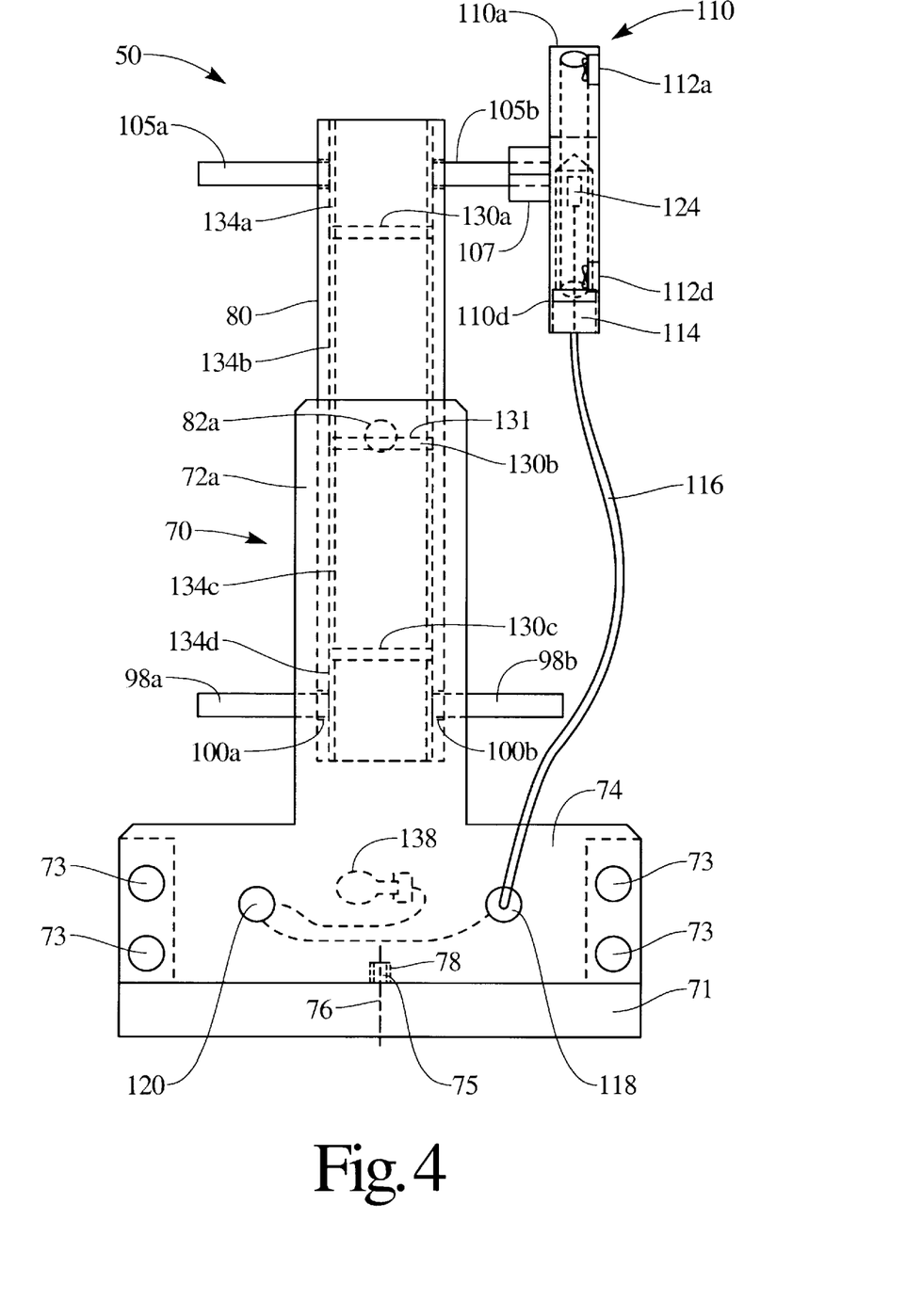
FIG. 4 is a side view of the microscope calibrator of FIG. 3.
Figure 5:
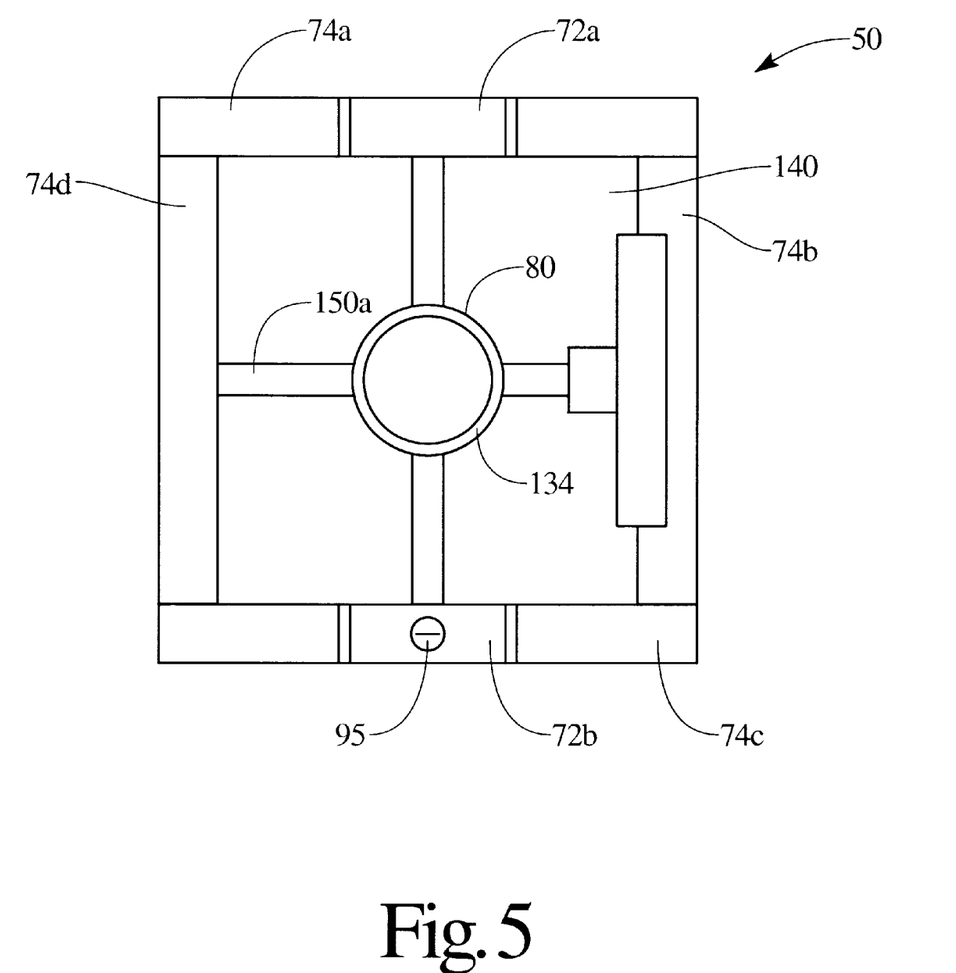
FIG. 5 is a top view of the microscope calibrator of FIG. 3.

Referring now to FIGS. 3, 4 and 5, the microscope calibrator 50 of the preferred embodiment is shown in more detail. A housing 70 made of aluminum or other structurally rigid material is rotatably situated on a platform 71. The housing includes a first side wall 72a, a second side wall 72b, and a base portion 74. The base portion 74 is made of four individual sections 74a, 74b, 74c, and 74d (see FIG. 5) each secured together using flat head screws 73. A rotation peg 75 protruding from a center point on the platform 72 is received by a mating rotation cavity 78 on a bottom side of the base portion 74 of the housing 70. The housing 70 is thereby capable of being rotated about an axis 76 defined by the rotation peg 75. Other electrical or mechanical means for rotatably mounting the housing 70 could alternatively be used.

A tubular shaft 80 is piviotably secured to the housing 70 via a pivot rod 82. The pivot rod 82 includes a first rod portion 82a interfacing with the first side wall 72a, and a second rod portion 82b interfacing with the second side wall 72b. The first rod portion 82a and second rod portion 82b are both centered along an axis of rotation 85. A first end 86a of the first rod portion 82a and a first end 86b of the second rod portion 82b are both rigidly attached to the shaft 80 by frictionally fitting the rod portions 82a, 82b into corresponding bores 88a, 88b in the shaft 80. The bores 88a, 88b each have an inner diameter sized to allow a tight frictional fit with the pivot rod 82. Glue or other adhesive material may also be provided in the bores 88a, 88b to better avoid slippage or other movements at this junction.

A second end 90a of the first rod portion 82a and a second end 90b of the second rod portion 82b are both rotatably secured to the housing 70. More specifically, the second end 90a of the first rod portion 82a is received by a bore 92a in the first side wall 72a of the housing 70. A diameter of the bore 92a is sized large enough that rotation of the first rod portion 82a may freely occur, yet small enough such that the rotation occurs smoothly and without wobble. The second end 90b of the second rod portion 82b is similarly situated within a bore 92b on the second side wall 72b. In order to adjust for rotational freedom of the shaft 80 about the axis 85, a tension screw 95 is provided. The tension screw 95 is situated within an aperture on a top side of the second side wall 72b. Of course, the tension screw 95 could additionally or alternatively be provided on the first side wall 72a or at other locations. An end 96 of the tension screw 95 may be adjusted such that it comes into contact with the second rod portion 82b through a nylon cloth (not shown). The nylon cloth aids in reducing frictional contact between the tension screw 95 and the second rod portion 82b such that this junction does not come to wear quickly in use. When the tension screw 95 is tightened with respect to the second rod portion 82b, the shaft 80 is fixed at its current location and cannot pivot freely about the axis 85. In this manner, the shaft 80 can be adjusted and secured by an operator to accommodate any desired pivotal angle.

In order to ensure easy movement of the shaft 80 about the axis 85, a pair of handles 98a, 98b are attached to the shaft 80. The handles 98a and 98b are each frictionally fit within handle receiving bores 100a, 100b, respectively, on the shaft 80. A diameter of each of the handle receiving bores 100a, 100b is such that the handles 98a and 98b cannot be rotated or removed during normal use and operation.

A support rod 105a, 105b is attached to the shaft 80 at an end of the shaft opposite the handles 98a, 98b. The support rods 105a and 105b are each capable of supporting location indicators such as a reference frame target 110 although in the present embodiment the target 110 is shown attached to support rod 105b. The target 110 attaches to the support rod 105b via a mechanical boss 107 which frictionally fits around the support rod 105b such that a secure fit is made and the target 110 is rigidly connected thereon. As best seen in FIG. 3, the target is shaped in the form of a cross having four arms 110a, 110b, 110c, and 110d, collectively referred to as arms 110. Disposed at an end of each of the arms 110 is a position signaling device 112a, 112b, 112c, 112d, collectively referred to as position signaling devices 112, such as an infrared emitter, a reflector, a sonic emitter, an RF emitter or other device. In the preferred embodiment, the position signaling devices are infrared emitters, however, other types of position signaling devices could be used depending on the type of cameras 22 in the operating room 12. Although the present embodiment shows four position signaling devices 112 it will be appreciated that only three such position signaling devices are needed for proper operations of the microscope calibrator 50 of the present embodiment. Additional position signaling devices 112 above three could be used to ensure proper tracking in the event one or more of the existing position signaling devices 112 fail or are blocked from view of the camera 22 for any reason or to provide redundancy.

The target 110 also includes an interfacing arm 112e (FIG. 3) in which power and other electrical signals may be provided to and from the target 110. An end of the interfacing arm includes a seven pin female connector 114. As best seen in FIG. 4, a cord 116 plugs in at one end to the connector 114 and at another end to a seven pin female connector 118 located on the base 74 of the housing 70. An internal cord 117 disposed in the base 74 of the housing 70 provides connection between the connector 118 and a connection pin 120. The connection pin 120 is located on the base 74 of the housing 70 and serves to provide a connection to the tool interface unit 55.

Also shown disposed in the target 110 and communicating through the cord 116 is a memory 124. The memory 124 is used to supply the tool interface unit 55 with a location of the signaling devices 112, the focusing targets 130, and other selected information relative to a selected point. The selected point from which the location of the signaling devices 112 are measured can be taken from any point, although in the preferred embodiment is taken from a center point 126 of signaling device 112a. The memory chip 124 is thereby able to supply the tool interface device 55 with a patterned orientation of the signaling devices 112 which the cameras 22 can later use to distinguish among multiple tools located in the operating room 12.

Figure 6:
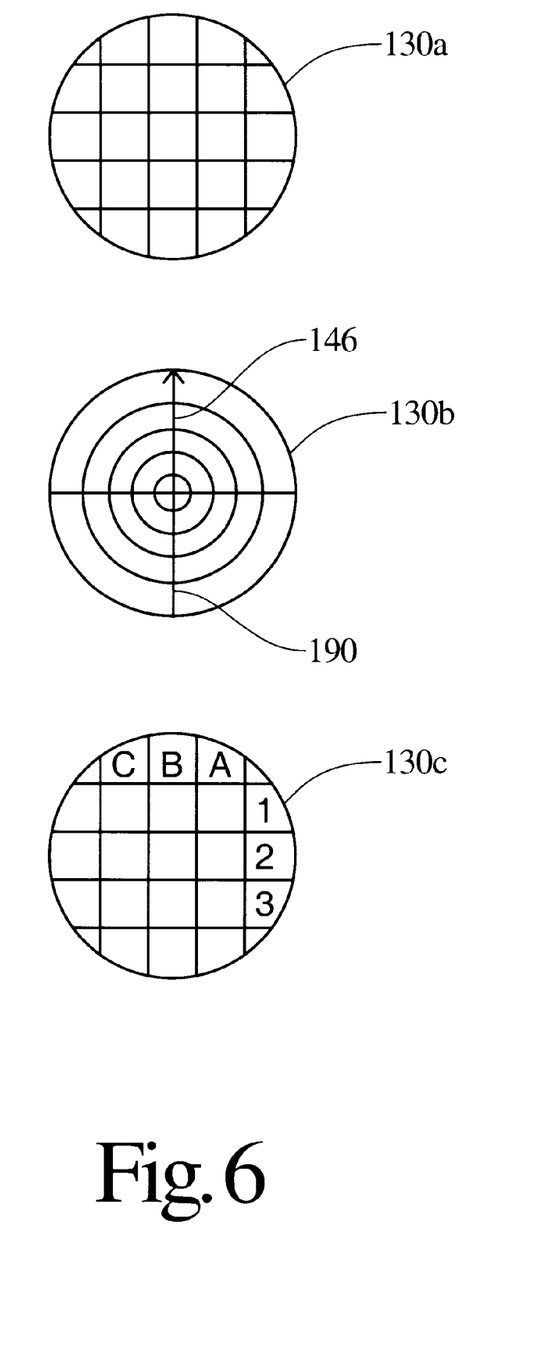
FIG. 6 is a top view of focusing targets in accordance with one embodiment of the present invention.

As best seen in FIGS. 4 and 6, located within the shaft 80 are three focusing targets 130a, 130b, 130c, collectively referred to as focusing targets 130. The focusing targets 130 of the present embodiment are each a glass reticle having a different target patterns printed thereon. Reticles of the present invention may, for instance, be selected from a variety of Edmond 27 mm Diameter Low reflection Chrome Contact Reticles, produced by Edmund Scientific Company in Barrington, N.J. The target patterns provide an operator viewing the focusing targets 130 through the microscope 35 with an image which can be focused upon. In order to better ensure that the operator viewing the focusing targets 130 does not accidently view the same target twice or otherwise mistakenly focus in on the wrong focusing target 130, each of the focusing targets of the present embodiment have a different target pattern.

The focusing targets 130 are each situated in the shaft 80 at a known predetermined location from one another. In order to secure the focusing targets 130 in place and ensure proper placement, a series of spacers 134a, 134b, 134c, 134d, collectively referred to as spacers 134, are used. The spacers 134 are cylindrically hollow studs with an outer diameter sized to snugly fit within an inner diameter of the shaft 80. The spacers 134 are each cut to a predetermined length to ensure that the focusing targets 130 are spaced a predetermined distance from one another. The spacers 134 are each secured in place within the shaft 80 using glue or other any other adhesive substance capable of securing the spacers 134 to the shaft 80. In the present embodiment, each of the focusing targets 130 are spaced at a distance of 50 mm from one another. However, any other appropriate distanced could be used depending on the type of microscope 35 in need of calibration. The focusing target 130b is located such that a top 131 of the focusing target 130b is aligned with the axis of rotation 85. Although the present embodiment shows three focusing targets 130a, 130b, 130c, only two focusing targets are needed for the present invention. The third and additional focusing targets are beneficial for double checking calibration and providing varying focal distances to handle a variety of microscope types.

In order to illuminate the target pattern on each focusing target 130, a light source 138 (FIG. 4) is provided within the base 74 of the housing 70. In the present embodiment, the light source 138 consists of two 0.5 watt incandescent bulbs although any number and size of light sources could be used to achieve a desired amount of illumination. Light from the light source 138 illuminates a light diffuser 140 (see FIG. 5). The light diffuser 140 of the present embodiment made of a frosted Lexan® material although other light diffusers could also be used. The light diffuser provides a relatively even distribution of light across the focusing targets 130 thereby allowing clear viewing from the microscope 35. Power and control for the light source 138 as well as the position signaling devices 112 are provided from the tool interface unit 55 via the connector 120.

Figure 7:
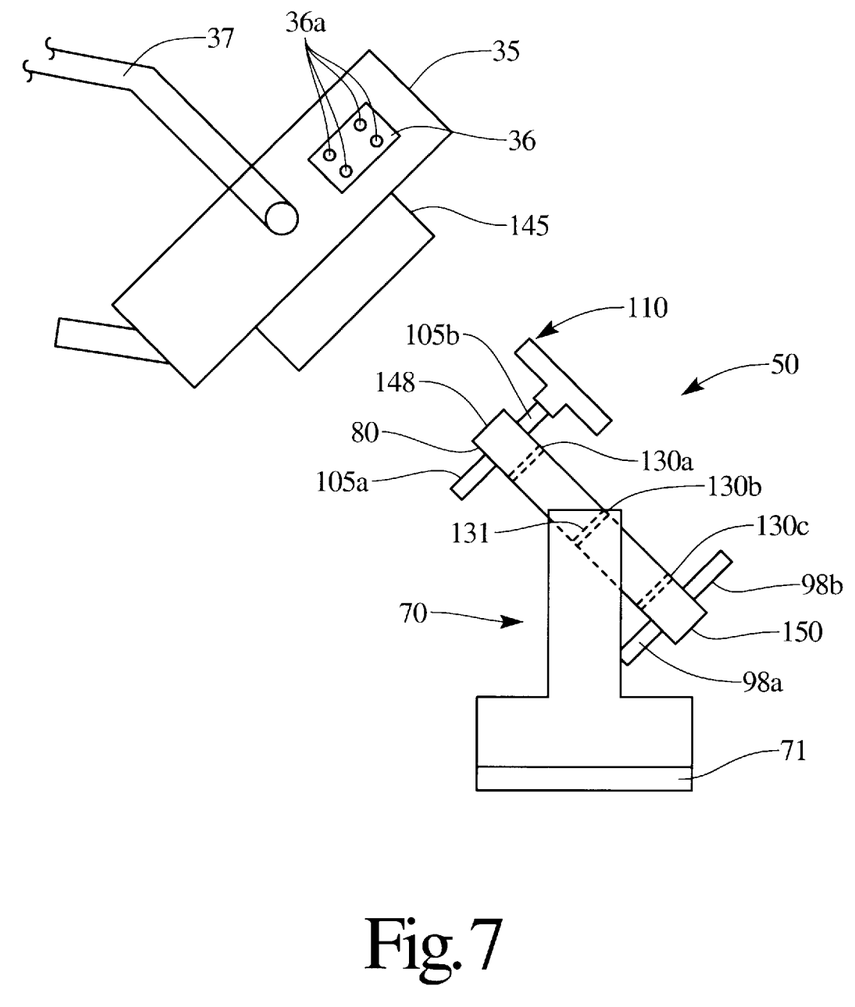
FIG. 7 is a side view of a microscope aligned with the microscope calibrator of FIG. 3.

Referring now to FIG. 7, the operations of the preferred embodiment of the invention will be discussed. The microscope calibrator 50 allows for rapidly determining attributes of the microscope 35. Attributes of the microscope 35 includes determining a focusing distance of the microscope lens such that a center of a depth of field can be determined, determining a rotational sense of the microscope such that images seen at the top, bottom, left and right of the microscope viewing field correspond to the orientation of an image on the viewable monitor, and determining a line of sight or barrel sight of the microscope with respect to the operating room. The tool calibrator 50 of the present invention is able to determine or verify calibration of the microscope 35 with respect to any and all of the above in a simple and easy manner.

In order to calibrate the microscope 35, the operator initially aligns a field of view seen through an eye piece 145 (see FIG. 1) of the microscope 35 with an open top end 148 of the shaft 80 closest to the target 110 such that a clear view down a center of the shaft 80 is available to the operator. In order to aid the operator in aligning the microscope 35, the entire microscope calibrator 50 may be moved along a surface upon which it is positioned. As discussed in more detail below, the entire microscope calibrator 50 may be moved to adjust for proper alignment with the microscope 35 during a time when the operator is focusing and adjusting for rotational sense with respect to the first focusing target, which in this case is focusing target 130b. Further the shaft 80 may be pivoted along its pivot rod 82 and the housing 70 may be rotated with respect to the platform 71.

Once adjusted, the operator continues the calibration by focusing on focusing target 130b. The operator knows if he or she is focused on the focusing target 130b, as opposed to focusing targets 130a or 130c, due to distinct target patterns provided on each of the focusing targets 130a, 130b, 130c. Next, the operator zooms the microscope in on the focusing target 130b such that a field of view seen through the eye piece 145 of the microscope only includes the focusing target 130b. Once completed, the operator adjusts the microscope calibrator 50 such that a top cross hair or other indicator mark seen through the eye piece 145 of the microscope 35 aligns with a top marking on the focusing target 130b. For instance, as shown in FIG. 6 the top marking on focusing target 130b is along a line 146 having an arrow indicating a top direction. A main reason for zooming in on the focusing target 130b is to ensure that the top cross hair of the microscope 35 properly aligned with the top marking of the focusing target 130b for purposes of calibrating a rotational sense of the microscope 35.

Once the operator has aligned the top cross hair of the microscope 35 with the top marking of the focusing target 130b, the operator next changes the focus of the microscope 35 such that the top focusing target 130a comes into focus. Depending on whether the microscope 35 has a fixed focusing distance or if the focusing distance is adjustable in nature, the operator may need to move the microscope 35 in order to bring the focusing target 130a into focus. If the microscope 35 is moved, the operator may find it necessary to reposition the shaft 80 of the microscope calibrator 50 in order to again have the shaft 80 align with the microscope 35. It will be appreciated, however, that during this re-alignment the entire microscope calibrator 50 should not be moved or rotated to re-align the microscope 35 with the focusing target 130a. Rather, only movements of the shaft 80 along pivot rod 82 should be made. This ensures that the top 131 of focusing target 130b which is aligned with the axis of rotation 85 (see FIG. 3) remains in a same relative position with respect to the local reference frame of the microscope calibrator 50 during such movements and ensures that the rotational alignments already made are not disrupted. Finally, the operator enters a command to the computer system 30 indicating calibration is taking place so that new information may be recorded or old calibration information may be verified.

The focusing distance of the microscope 35 is calibrated in the above mentioned calibration steps by virtue of the cameras 22 (FIG. 1) sensing a location of both the position signaling devices 36*a* attached to the microscope 35 and a location of the position signaling devices 52 of the tool calibrator 50 at a point in which the operator enters the command to the computer system 30 to calibrate. It will be appreciated that the determination of the focusing distance of the microscope 35 by the computer system 30 is based only on the microscope 35 having focused on one of the focusing targets 130 which in the present embodiment is focusing target 130*a*.

More specifically, in the present embodiment the computer system 30 is preprogrammed to assume that the microscope is focused on focusing target 130*a* when the operator enters the command to the computer system 30 indicating calibration is taking place. By sensing a location of the position signaling devices 52 attached to the microscope calibrator 50 and knowing an offset between a selected point with respect to the position signaling devices 52 and a location of the top focusing target 130*a* by way of the memory 124, the computer system is able to determine the location of focusing target 130*a* with respect to the position signaling devices 52 and thus with respect to the operating room 12 reference frame. Next, by comparing a sensed location of the position signaling devices 36 connected to the microscope with the determined location of the focusing target 130*a* the computer system 30 is able to determine, record and establish the focusing distance of the microscope 35.

The rotational sense of the microscope 35 may be determined or verified by virtue of aligning the top cross hair of the microscope 35 with the top marking of the focusing target 130*b* and sensing a location of the position signaling devices 52 of the tool calibrator at the point in which the operator enters the command to the computer system 30 to calibrate. More specifically, by having stored in the memory 124 the orientation of the top marking of the focusing target 130*b* with respect to the position signaling devices 52, the computer system 30 is able to determine which direction the top marking of the focusing target 130*b* is facing with respect to the operating room reference frame during calibration. Even thought the microscope 35 is focused on focusing target 130*a* at the point in which the computer system 30 is told to calibrate, the microscope calibrator 50 should not have been rotated from the point at which the microscope 35 focused on focusing target 130*b* and established a rotational sense as discussed above. Thus, by comparing a position of the position signaling devices 36*a* attached to the microscope 35 with the position of the top marking of the focusing target 130*b* at the point at which the computer system 30 is told to calibrate, the computer system 30 is able to determine, record and establish the rotational sense of the microscope. More specifically, the computer system 30 orients images shown on monitors 31 such that what is shown on the top, bottom, left and right of the monitors 31 correspond to an orientation in which the operator is viewing through the microscope eye piece 145. Further, as the microscope 35 is physically moved in the operating room 12, the computer system 30 can adjust images on the screen to correspond to a current positioning of the microscope. It will be appreciated, that although the present embodiment describes aligning the top cross hair of the microscope 35 with the top marking of the focusing target 130*b* to determine the rotational sense, it is also possible to use any other focusing target 130 to align rotational sense, and this determination could be done independent of any other calibration of the microscope 35.

The line of sight or barrel sight of the microscope 35 is determined by virtue of the computer system 30 calculating a vector between a center point of the top 131 of the focusing target 130*b* and a sensed position of a center point of a top surface of the focusing target 130*a*. As the computer system 30 is preprogrammed to assume an operator of the microscope 35 has focused on these two points, the line of sight of the microscope 35 coincides with the direction of the vector calculated between the same points. Because the memory 124 of the tool calibrator 50 has stored offset values between the position signaling devices 52 of the tool calibrator 50 and each of these points on focusing targets 130*a*, 130*b*, respectively, a location of the vector between these two points can be calculated with respect to the position signaling devices 52 at the time of calibration. It will be appreciated that since focusing target 130*b* is aligned with the axis of rotation 85 of the shaft 80, movements made to the microscope calibrator 50 during re-alignment of the microscope 35 with focusing target 130*a* does not change the relative location of the center point of focusing target 130*b* with respect to the position signaling devices 52 of the tool calibrator 50. As such, the operator need only determine the positioning of the microscope 35 with respect to the tool calibrator 50 at one time during the calibration process. If focusing target 130*b* was not aligned with the axis of rotation 85, then movements to the shaft 80 done to re-align the microscope 35 with the focusing target 130*a* would have also made the location of the center point of focusing target 130*b* change with respect to the position signaling devices 52 of the microscope calibrator 50. As such, the operator would not have been able to enter a single calibrate command to the computer system 30 to calculate the line of sight, but rather, would have had to determine the location of the microscope 35 and microscope calibrator 50 when the microscope 35 was focusing on focusing target 130*b* as well as when it was focusing on focusing target 130*a*.

Figure 8:
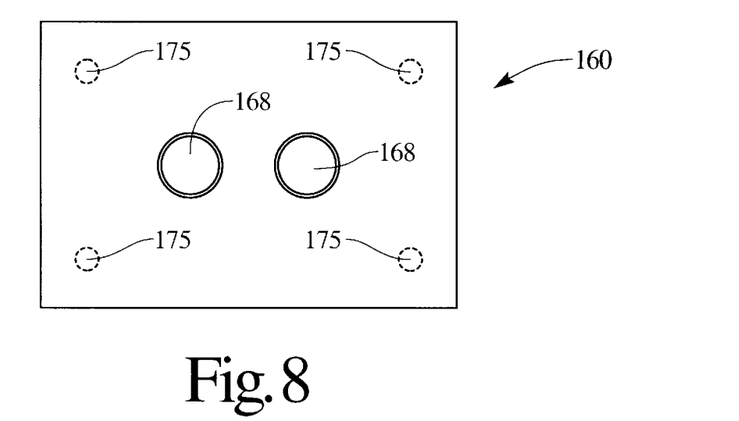
FIG. 8 is a top view of a microscope calibrator in accordance with another embodiment of the present invention.
Figure 9:
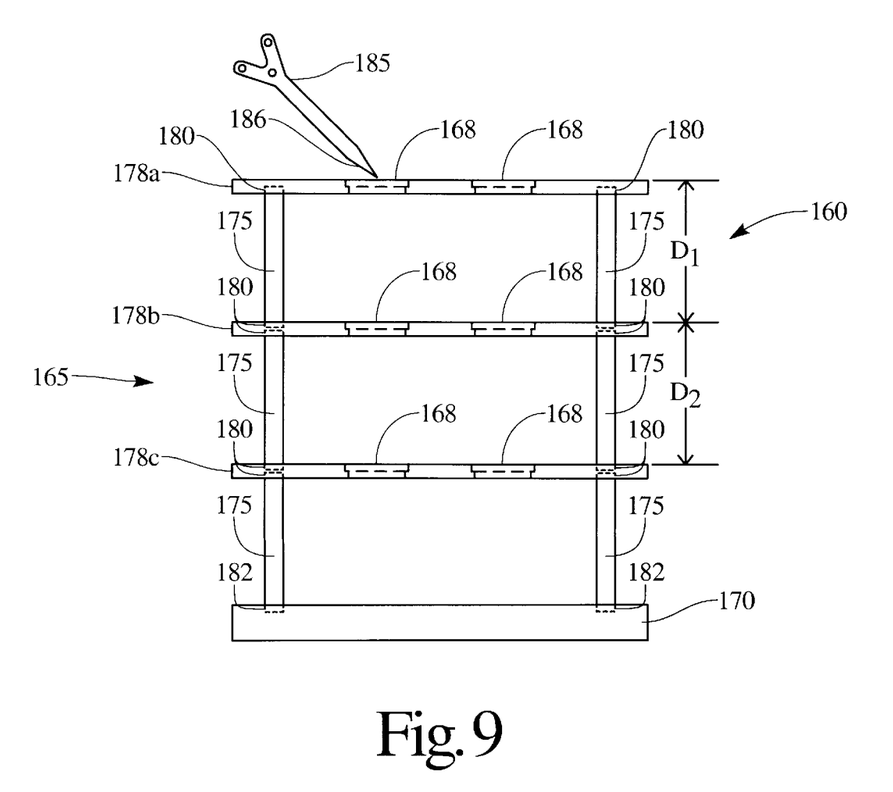
FIG. 9 is a front view of the microscope calibrator of FIG. 8.

Referring now to FIGS. 8 and 9, an alternative embodiment of the present invention is shown. A microscope calibrator 160 of the present embodiment includes a housing 165 supporting focusing targets 168. The housing 165 includes a base portion 170 and a plurality of support rods 175. The housing 165 further includes platform layers 178*a*, 178*b*, and 178*c*, collectively referred to as platform layers 178, each supported by support rods 175. The platforms layers 178 are each made of Lexan and include grooved circular apertures in which the focusing targets 168 are situated. In the present embodiment, each platform layer 178 includes two focusing targets 168, however any number of focusing targets 168 could be used. The focusing targets 168 are reticles such as those shown in FIG. 6, however, any type of focusing target upon which the microscope 35 can focus could alternatively be used.

Each support rod 175 is pressed fit into a corresponding bore 180 in an adjacent platform layer 178. Further, each support rods 175 adjacent the base 170 are press fit into corresponding bores 182 in the base 170. A diameter of each of the bores 180, 182 are sized just slightly larger than a diameter of each support rod 175 such that a secure frictional fit is made. A length of each of the support rods 175 is precisely cut such that each platform layer 178 is situated at desired distances D1, D2 from one another. In the present embodiment, the distances D1 and D2 are each 50 mm although any desired distance could be used.

In order to calibrate the microscope 35 in the present embodiment, the operator situates the microscope 35 above the microscope calibrator 160 and initially focuses the eye piece 145 on one of the focusing targets 168 on platform layer 178*b*. Once focusing is achieved, the operator takes a tracked probe 185 such as probe 60 (see FIG. 1) and places a tip 186 of the probe 185 at a center point of the focusing target 168. Two focusing targets 168 are provided on each platform layer 178 so that both right handed and left handed individuals may easily reach the focusing target 168 with the tracked probe 185. By using the tracked probe 185, the position of the focusing target 168 upon which the operator focused the microscope 35 can be determined by the computer system 30. Next, the operator focuses the eye piece 145 of the microscope on one of the focusing targets 168 on the platform layer 178*c*. Once again, once focusing in achieved, the operator takes the tracked probe 185 and places the tip 186 of the probe 185 at a center point on the focusing target 168. The operator could optionally follow similar steps with respect to focusing targets 168 on platform layer 178*a*, however, this is not necessary to properly calibrate the microscope 35 but could serve as a double check. The order and selection of focusing targets 168 on which to focus is also fully optional so long as focusing targets 168 on two different platform layers 178 are eventually focused upon and the location of each focusing target 168 is captured via tracked probe 185. Upon completion of these steps the focusing distance and line of sight of the microscope 35 can be calculated by the computer system 30.

Although the above procedure is sufficient to calibrate the center point of the depth of field of the microscope 35 and the line of sight or barrel sight of the microscope 35, one additional step is needed to calibrate the rotational sense. Specifically, in order to also calibrate the rotational sense of the microscope, the operator focuses the eye piece 145 of the microscope on a cross hair off center from one the focusing target 168 the operator focused upon. For instance, as shown in FIG. 6, a point 190 on the focusing target 130*b* could be selected. Upon focusing on this point 190, the operator once again places a tip of the tracked probe 185 on the point 190. With this information, the computer system 30 has sufficient information to determine the rotational sense of the microscope 35 as is known in the art.

Figure 10:
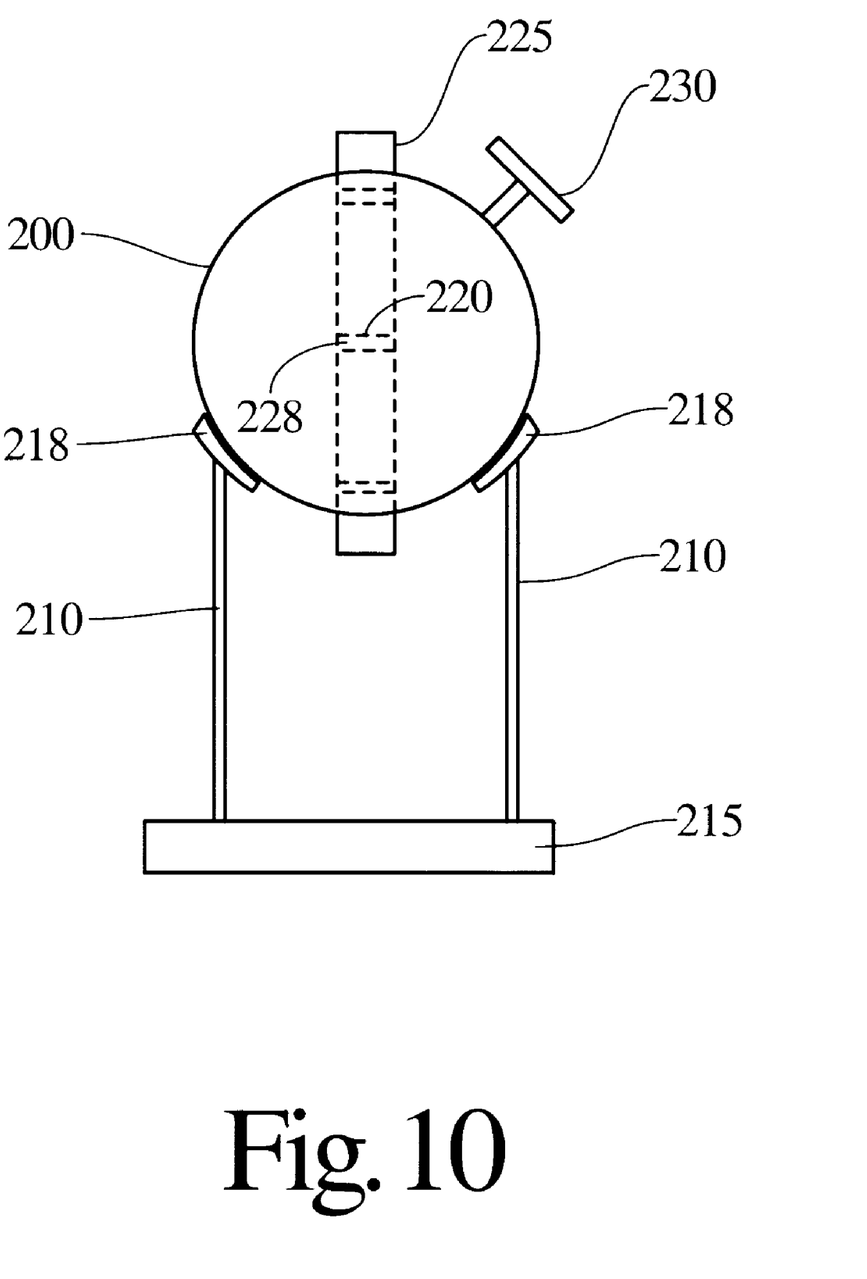
FIG. 10 is a front view of a microscope calibrator in accordance with yet another embodiment of the present invention.

Referring to FIG. 10, another embodiment of the present invention is shown. In this embodiment, a spherical ball 200 is shown to be supported by support rods 210. The support rods 210 are attached at one end to a base 215 and at an other end to ball support pads 218. The ball support pads 218 allow the spherical ball 200 to rotate about its center point 220.

A shaft 225 is positioned through a center of the spherical ball 200 and secured into position using an adhesive material or connected using screws or in some other way. The shaft 225 is substantially the same as the shaft 80 shown in FIG. 3 except that it is mounted to the spherical ball 200 and a center focusing target 228 disposed in the shaft 225 is located such that a top of the focusing target 228 is aligned with the center point 220 of the spherical ball 200. Further a reference frame target 230 is affixed to the spherical ball and includes three or more position signaling devices similar to the reference frame target 110. The operations of the microscope calibrator shown in FIG. 10 are substantially identical to the operations of the microscope calibrator 50 described above except that movement of the shaft 225 occurs by rotating the spherical ball 200 along the ball support pads 218.

The invention has been described with reference to the preferred embodiments. Obviously, modifications and alterations will occur to others upon reading and understanding the preceding detailed description. The It is intended that the invention be construed as including all such modifications and alterations insofar as they come within the scope of the appended claims or their equivalence thereof.

What is claimed is:

1. An apparatus comprising:
   a first focusing target;
   a second focusing target disposed in a spaced relationship to the first focusing target;
   a support adapted to hold the focusing target within the field of view of a surgical microscope, wherein the support includes a member defining an aperture having a longitudinal axis and the first focusing target and second focusing target are situated along the longitudinal axis; and
   means for communicating the location of the focusing target to a processor.

2. The apparatus of claim 1 further including a third focusing target disposed in spaced relation to the first and second focusing targets.

3. The apparatus of claim 1 wherein the member is supported for pivotable movement about a pivot axis and the pivot axis is perpendicular to the longitudinal axis of the member.

4. The apparatus of claim 3 wherein the first focusing target is situated on the pivot axis.

5. A method of calibrating a surgical microscope, the method comprising the steps of:
   focusing the surgical microscope on a focusing target;
   communicating the location of the focusing target to a processor;
   communicating the location of the surgical microscope to the processor; and
   determining at least one attribute of the surgical microscope using the communicated locations of the focusing target and surgical microscope.

6. The method of claim 5 further including the steps of focusing the microscope on a second focusing target and communicating the location of the second target to the processor.

7. The method of claim 5 further including the step of storing data in a memory correlating the location of the focusing target to a position indicator associated with the focusing target.

8. The method of claim 1 further including the steps of accessing a memory mounted proximate to the focusing target, the memory containing the stored data and providing the stored data to the processor.

9. The method of claim 7 wherein the step of communicating further includes the step of establishing a localized reference system for sensing the location of the position indicator associated with the focusing target.

\* \* \* \* \*